(12) United States Patent
Taylor et al.

(10) Patent No.: US 9,700,444 B2
(45) Date of Patent: Jul. 11, 2017

(54) MODIFIED PUSHER APPARATUS

(71) Applicant: BIU BIOMEDICAL INNOVATIONS (UROLOGY) INC., Vancouver (CA)

(72) Inventors: William N. Taylor, Vancouver (CA); Ian T. McDougall, Vancouver (CA)

(73) Assignee: BIU BIOMEDICAL INNOVATIONS (UROLOGY) INC., Vancouver, British Columbia (CA)

( * ) Notice: Subject to any disclaimer, the term of this patent is extended or adjusted under 35 U.S.C. 154(b) by 0 days.

(21) Appl. No.: 14/401,933

(22) PCT Filed: May 3, 2013

(86) PCT No.: PCT/CA2013/000438
§ 371 (c)(1),
(2) Date: Nov. 18, 2014

(87) PCT Pub. No.: WO2013/170349
PCT Pub. Date: Nov. 21, 2013

(65) Prior Publication Data
US 2015/0182362 A1 Jul. 2, 2015

Related U.S. Application Data

(60) Provisional application No. 61/649,102, filed on May 18, 2012.

(51) Int. Cl.
*A61F 2/95* (2013.01)
*A61F 2/94* (2013.01)
(Continued)

(52) U.S. Cl.
CPC .................. *A61F 2/95* (2013.01); *A61F 2/82* (2013.01); *A61F 2/94* (2013.01); *A61F 2/966* (2013.01);
(Continued)

(58) Field of Classification Search
CPC .... A61F 2/94; A61F 2/95; A61F 2/966; A61F 2002/048; A61F 2002/041;
(Continued)

(56) References Cited

U.S. PATENT DOCUMENTS 5,141,502 A 8/1992 Macaluso, Jr.
5,147,370 A * 9/1992 McNamara ............... A61F 2/88
606/108

(Continued)

FOREIGN PATENT DOCUMENTS

CA 2107478 A1 10/1992
WO WO 92/17111 A1 10/1992
(Continued)

OTHER PUBLICATIONS

Krauthamer, Richard. "A Simplified Method for Antegrade Ureteral Stent Placement," *AJR*, Apr. 1991, 156:763-764.

*Primary Examiner* — Alexander Orkin
(74) *Attorney, Agent, or Firm* — Saliwanchik, Lloyd & Eisenschenk (57) ABSTRACT

Placement of a stent having a tethered ferromagnetic bead may be facilitated with a modified pusher having an opening at the distal end of the pusher to receive the tethered ferromagnetic bead. The ferromagnetic bead may be positioned within the bladder whereby a tether connection to a shortened stent ending within the ureter may be used to reduce the likelihood of patient irritation. The bead, tether, and stent assembly may be advanced into the patient as a unit along a conventional guide wire and using a conventional cystoscope.

12 Claims, 5 Drawing Sheets

(51) Int. Cl.
*A61F 2/966* (2013.01)
*A61F 2/82* (2013.01)
*A61F 2/04* (2013.01)
*A61M 27/00* (2006.01)

(52) U.S. Cl.
CPC ... *A61F 2002/041* (2013.01); *A61F 2002/048* (2013.01); *A61F 2220/0075* (2013.01); *A61F 2250/0029* (2013.01); *A61M 27/008* (2013.01)

(58) Field of Classification Search
CPC ...... A61F 2002/9528; A61F 2002/9665; A61F 2002/9534; A61F 2002/9511; A61B 17/12113; A61B 17/12118; A61M 27/008
See application file for complete search history.

(56) References Cited

U.S. PATENT DOCUMENTS

| | | | |
|---|---|---|---|
| 5,159,920 A | 11/1992 | Condon et al. | |
| 5,322,501 A | 6/1994 | Mahmud-Durrani | |
| 5,372,600 A * | 12/1994 | Beyar | A61F 2/95 606/194 |
| 5,800,455 A * | 9/1998 | Palermo | A61B 17/12022 606/108 |
| 5,833,694 A | 11/1998 | Poncet | |
| 6,258,098 B1 | 7/2001 | Taylor et al. | |
| 6,319,287 B1 | 11/2001 | Frimberger | |
| 6,652,569 B1 | 11/2003 | Taylor et al. | |
| 7,550,002 B2 | 6/2009 | Goto et al. | |
| 7,758,624 B2 | 7/2010 | Dorn et al. | |
| 7,918,800 B1 * | 4/2011 | Brown | A61B 5/061 600/300 |
| 8,034,094 B2 | 10/2011 | Aoba et al. | |
| 8,075,606 B2 | 12/2011 | Dorn | |
| 8,092,509 B2 | 1/2012 | Dorn et al. | |
| 8,758,369 B2 * | 6/2014 | Selis | A61B 19/54 600/431 |
| 2005/0059890 A1 * | 3/2005 | Deal | A61B 1/018 600/433 |
| 2005/0119722 A1 * | 6/2005 | Styrc | A61F 2/95 623/1.12 |
| 2005/0137699 A1 * | 6/2005 | Salahieh | A61F 2/2418 623/2.11 |
| 2007/0208302 A1 * | 9/2007 | Webster | A61M 25/0041 604/103.04 |
| 2008/0300616 A1 * | 12/2008 | Que | A61B 17/12022 606/191 |
| 2012/0095567 A1 * | 4/2012 | Weisman | A61F 2/95 623/23.7 |

FOREIGN PATENT DOCUMENTS

| | | |
|---|---|---|
| WO | WO 99/58083 A1 | 11/1999 |
| WO | WO 03/011192 A2 | 2/2003 |
| WO | WO 2011/086175 A1 | 7/2011 |

* cited by examiner

MODIFIED PUSHER APPARATUS

RELATED APPLICATIONS

This application is a National Stage Application of International Application Number PCT/CA2013/000438, filed May 3, 2013; which claims priority to U.S. provisional patent application Ser. No. 61/649,102, filed May 18, 2012; which are incorporated herein by reference in their entirety.

TECHNICAL FIELD

This invention relates to the field of stent placement, where the stent may be used to keep open body channels. In particular, the invention relates to a stent placement pusher apparatus.

BACKGROUND

Stents are used to keep open body channels. For example, ureteral stents may provide drainage of urine from the kidneys to the bladder. Similarly, biliary stents may provide drainage of the bile ducts between the liver and gallbladder and between the gallbladder and small intestine. A stent is a flexible, tubular structure that is made from relatively inert materials (for example, silicon, Teflon™, polyethylene, polyurethane, stainless steel, or nickel-titanium alloy). Often a stent may be perforated to provide small drainage holes along its length. Stents may also be shaped to define "hooks" at either end. For example, such hooks may prevent migration of a ureteral stent from the kidney toward the bladder or from the bladder upwards. A shortened ureteral stent has only one hook at the distal or kidney end of the stent. Often, shortened stents are used to reduce irritation caused by the presence of a stent within the lower ureter and within the bladder. With a shortened stent, the stent resides in the ureter, remote from the bladder and the ureteral orifice (i.e. the junction of the ureter and the bladder).

Indwelling stents periodically need to be removed or periodically replaced. Conventional stent removal procedures may be complex and may be painful, sometimes requiring general anesthesia.

A thin thread may be attached to a shortened stent to extend into the bladder to assist with the removal of the stent. However, such a shortened stent (with thread) requires endoscopic visualization of the threads so that they may be grasped, and the stent may be withdrawn.

Although this is a relatively simple procedure, it requires specialized instruments used by an urologist in a sterile setting. Nevertheless, general anesthesia may also be required.

An alternative stent removal method is described in WO 99/58083, which employs the use of a tethered bead at the proximal or bladder end of the stent that may be removed with the aid of magnet tipped catheter.

SUMMARY

The pusher apparatus or pusher attachment apparatus attached to a pusher described herein allow for the insertion of a shortened stent (the stent having a bead suspended by a tether) into a patient's ureter 90 without the need for a positioning line to withdraw the bead from the ureter 90 during positioning of the stent. Using the modified pusher apparatus described herein or pusher attachment apparatus attached to a pusher, the bead does not need to be pushed past the ureteral orifice 85 and into the ureter 90, but remains within the pusher receptacle 17 and can stay within the bladder. Accordingly, the pusher apparatus described herein may reduce irritation to the patient's ureter and simplify the insertion, when used with a shortened stent with a tethered bead.

In accordance with one embodiment, there is provided an apparatus for the insertion of a shortened stent, said stent having a bead suspended by a tether, wherein, the pusher includes: (a) a hollow tube having a distal end and a proximal end; and (b) an opening defined in the peripheral wall of the pusher near the distal end, which reaches the inner hollow portion of the pusher and may be sized to allow for the positioning of the bead into the opening and at least partially within the receptacle defined by the opening.

In accordance with another embodiment, there is provided a pusher apparatus, for the insertion of a shortened stent, said stent having a bead suspended by a tether, wherein, the pusher includes: (a) a hollow tube having a distal end and a proximal end; and (b) an opening defined in the peripheral wall of the pusher near the distal end, which extends into the inner hollow portion of the pusher and may be sized to allow for the positioning of the bead into the opening and at least partially within the receptacle defined by the opening.

In accordance with another embodiment, there is provided a pusher apparatus, for the insertion of a shortened stent, said stent having a bead suspended by a tether, wherein, the pusher includes: (a) a hollow tube having a distal end and a proximal end; and (b) an opening defined in the peripheral wall of the pusher near the distal end, which reaches the inner hollow portion of the pusher and may be sized to allow for the positioning of the bead through the opening and within the receptacle defined by the opening.

In accordance with another embodiment, there is provided a pusher apparatus, for the insertion of a shortened stent, said stent having a bead suspended by a tether, wherein, the pusher includes: (a) a hollow tube having a distal end and a proximal end; and (b) an opening defined in the peripheral wall of the pusher near the distal end, which reaches the inner hollow portion of the pusher and may be sized to allow for the positioning of the bead through the opening and within the pusher.

In accordance with another embodiment, there is provided a pusher apparatus, including: (a) a hollow tube with a distal end and a proximal end; and (b) an opening defined in the peripheral wall of the pusher near the distal end, which reaches the inner hollow portion of the pusher and may be sized to allow for positioning of a tethered bead into the opening and at least partially within the pusher.

In accordance with another embodiment, there is provided a pusher attachment apparatus, including: (a) a hollow tube having a distal end and a proximal end; (b) a connector at the proximal end of the hollow tube for attachment to a pusher having a lumen, whereby the lumen of the pusher may be contiguous with the lumen of the hollow tube; and (c) an opening defined in the peripheral wall of the hollow tube, which extends to the inner hollow portion of the hollow tube and may be sized to allow for positioning of a tethered bead into the opening and at least partially within the receptacle defined by the opening.

In accordance with another embodiment, there is provided a pusher attachment apparatus, including: (a) a hollow tube having a distal end and a proximal end; (b) a connector at the proximal end of the hollow tube for attachment to a pusher having a lumen, whereby the lumen of the pusher may be contiguous with the lumen of the hollow tube; and (c) an opening defined in the peripheral wall of the hollow tube, which reaches the inner hollow portion of the hollow tube and may be sized to allow for positioning of a tethered bead into the opening and at least partially within the pusher attachment apparatus.

In accordance with another embodiment, there is provided a commercial package including: (a) a guide wire over which a stent may be pushed; (b) a stent assembly for keeping open body channels and having a tethered bead for stent retrieval, the stent and bead being adapted to be pushed over the guide wire; (c) a pusher attachment, as described herein, adapted to be pushed over the guide wire to advance the stent relative to the guide wire and to accept the tethered bead within the opening; and (d) a pusher tube adapted to be pushed over the guide wire for advancing the stent relative to the guide wire.

In accordance with another embodiment, there is provided a commercial package comprising: (a) a guide wire over which a stent may be pushed; (b) a stent assembly for keeping open body channels and having a tethered bead for stent retrieval, the stent and bead being adapted to be pushed over the guide wire; and (c) a pusher apparatus, as described herein, adapted to be pushed over the guide wire to advance the stent relative to the guide wire and to accept the tethered bead into the opening.

The guide wire, the stent assembly, the pusher attachment, and the pusher tube may be for use in delivering the stent assembly to a human ureter. The guide wire, the stent assembly, and the pusher apparatus may be for use in delivering the stent assembly to a human ureter.

The outer diameter of the hollow tube may be less than the diameter of the bead, provided that the pusher apparatus with a bead positioned within the receptacle is able to pass through the lumen of a cytoscope. The outer diameter of the hollow tube may be approximately the diameter of the bead. The outer diameter of the hollow tube may be greater than the diameter of the bead.

Alternatively, the outer diameter of the hollow tube may be greater than the diameter of the bead plus the cross-sectional area of the peripheral wall of the pusher opposite the opening. The outer diameter of the hollow tube may be less than the diameter of the bead plus the cross-sectional area of the peripheral wall of the pusher opposite the opening, provided that the pusher apparatus with a bead positioned within the receptacle is able to pass through the lumen of a cytoscope. The outer diameter of the hollow tube may be approximately the diameter of the bead plus the cross-sectional area of the peripheral wall of the pusher opposite the opening.

The opening may be greater than 180° of the circumference of the pusher. The opening may be greater than 185° of the circumference of the pusher. The opening may be greater than 190° of the circumference of the pusher. The opening may be greater than 195° of the circumference of the pusher. The opening may be greater than 200° of the circumference of the pusher. The opening may be greater than 205° of the circumference of the pusher. The opening may be greater than 210° of the circumference of the pusher. The opening may be greater than 210° of the circumference of the pusher. The opening may be greater than 215° of the circumference of the pusher. The opening may be greater than 220° of the circumference of the pusher. The opening may be greater than 225° of the circumference of the pusher. The opening may be greater than 230° of the circumference of the pusher. The opening may be greater than 235° of the circumference of the pusher. The opening may be greater than 240° of the circumference of the pusher. The opening may be greater than 250° of the circumference of the pusher. The opening may be greater than 255° of the circumference of the pusher. The opening may be greater than 260° of the circumference of the pusher. The opening may be greater than 265° of the circumference of the pusher. The opening may be greater than 270° of the circumference of the pusher. The opening may be greater than 280° of the circumference of the pusher. The opening may be greater than 285° of the circumference of the pusher. The opening may be greater than 290° of the circumference of the pusher. The opening may be greater than 295° of the circumference of the pusher. The opening may be greater than 300° of the circumference of the pusher. The opening may be greater than 305° of the circumference of the pusher. The opening may be greater than 310° of the circumference of the pusher. The opening may be greater than 315° of the circumference of the pusher. The opening may be greater than 320° of the circumference of the pusher. The opening may be greater than 325° of the circumference of the pusher. The opening may be greater than 330° of the circumference of the pusher. The opening may be greater than 335° of the circumference of the pusher. The opening may be greater than 340° of the circumference of the pusher. The opening may be greater than 345° of the circumference of the pusher. The opening may be greater than 350° of the circumference of the pusher. The opening may be greater than 355° of the circumference of the pusher.

The area adjacent the opening may be reinforced to maintain structural integrity of the pusher tube. The reinforcement may be by the addition of a material that is less flexible than the pusher. The reinforcement may be by the use of a material that is less flexible than the pusher tube adjacent the opening.

The minimum distance between the distal end of the pusher and the opening may be about 3 cm. The minimum distance between the distal end of the pusher and the opening may be about 2.5 cm. The minimum distance between the distal end of the pusher and the opening may be about 5.0 cm. The minimum distance between the distal end of the pusher and the opening may be about 4.9 cm. The minimum distance between the distal end of the pusher and the opening may be about 4.8 cm. The minimum distance between the distal end of the pusher and the opening may be about 4.7 cm. The minimum distance between the distal end of the pusher and the opening may be about 4.6 cm. The minimum distance between the distal end of the pusher and the opening may be about 4.5 cm. The minimum distance between the distal end of the pusher and the opening may be about 4.4 cm. The minimum distance between the distal end of the pusher and the opening may be about 4.3 cm. The minimum distance between the distal end of the pusher and the opening may be about 4.2 cm. The minimum distance between the distal end of the pusher and the opening may be about 4.1 cm. The minimum distance between the distal end of the pusher and the opening may be about 4.0 cm. The minimum distance between the distal end of the pusher and the opening may be about 3.9 cm. The minimum distance between the distal end of the pusher and the opening may be about 3.8 cm. The minimum distance between the distal end of the pusher and the opening may be about 3.7 cm. The minimum distance between the distal end of the pusher and the opening may be about 3.6 cm. The minimum distance between the distal end of the pusher and the opening may be about 3.5 cm. The minimum distance between the distal end of the pusher and the opening may be about 3.4 cm. The minimum distance between the distal end of the pusher and the opening may be about 3.3 cm. The minimum distance between the distal end of the pusher and the opening may be about 3.2 cm. The minimum distance between the distal end of the pusher and the opening may be about 3.1 cm. The minimum distance between the distal end of the pusher and the opening may be about 2.9 cm. The minimum distance between the distal end of the pusher and the opening may be about 2.8 cm. The minimum distance between the distal end of the pusher and the opening may be about 2.7 cm. The minimum distance between the distal end of the pusher and the opening may be about 2.6 cm. The minimum distance between the distal end of the pusher and the opening may be about 2.4 cm. The minimum distance between the distal end of the pusher and the opening may be about 2.3 cm. The minimum distance between the distal end of the pusher and the opening may be about 2.2 cm. The minimum distance between the distal end of the pusher and the opening may be about 2.1 cm. The minimum distance between the distal end of the pusher and the opening may be about 2.0 cm. The minimum distance between the distal end of the pusher and the opening may be about 1.9 cm. The minimum distance between the distal end of the pusher and the opening may be between about 4 cm and 10 cm. The minimum distance between the distal end of the pusher and the opening may be between about 5 cm and 8 cm. The minimum distance between the distal end of the pusher and the opening may be between about 5 cm and 10 cm. The minimum distance between the distal end of the pusher and the opening may be between about 5 cm and 9 cm. The minimum distance between the distal end of the pusher and the opening may be between about 5 cm and 7 cm. The minimum distance between the distal end of the pusher and the opening may be between about 5 cm and 6 cm. The minimum distance between the distal end of the pusher and the opening may be between about 4 cm and 10 cm. The minimum distance between the distal end of the pusher and the opening may be between about 4 cm and 9 cm. The minimum distance between the distal end of the pusher and the opening may be between about 4 cm and 8 cm. The minimum distance between the distal end of the pusher and the opening may be between about 4 cm and 7 cm. The minimum distance between the distal end of the pusher and the opening may be between about 4 cm and 6 cm. The minimum distance between the distal end of the pusher and the opening may be between about 3 cm and 12 cm. The minimum distance between the distal end of the pusher and the opening may be between about 3 cm and 11 cm. The minimum distance between the distal end of the pusher and the opening may be between about 3 cm and 10 cm. The minimum distance between the distal end of the pusher and the opening may be between about 3 cm and 9 cm. The minimum distance between the distal end of the pusher and the opening may be between about 3 cm and 8 cm. The minimum distance between the distal end of the pusher and the opening may be between about 2 cm and 10 cm.

The minimum distance between the distal end of the pusher attachment and the opening may be about 3 cm. The minimum distance between the distal end of the pusher attachment and the opening may be about 2.5 cm. The minimum distance between the distal end of the pusher attachment and the opening may be about 5.0 cm. The minimum distance between the distal end of the pusher attachment and the opening may be about 4.9 cm. The minimum distance between the distal end of the pusher attachment and the opening may be about 4.8 cm. The minimum distance between the distal end of the pusher attachment and the opening may be about 4.7 cm. The minimum distance between the distal end of the pusher attachment and the opening may be about 4.6 cm. The minimum distance between the distal end of the pusher attachment and the opening may be about 4.5 cm. The minimum distance between the distal end of the pusher attachment and the opening may be about 4.4 cm. The minimum distance between the distal end of the pusher attachment and the opening may be about 4.3 cm. The minimum distance between the distal end of the pusher attachment and the opening may be about 4.2 cm. The minimum distance between the distal end of the pusher attachment and the opening may be about 4.1 cm. The minimum distance between the distal end of the pusher attachment and the opening may be about 4.0 cm. The minimum distance between the distal end of the pusher attachment and the opening may be about 3.9 cm. The minimum distance between the distal end of the pusher attachment and the opening may be about 3.8 cm. The minimum distance between the distal end of the pusher attachment and the opening may be about 3.7 cm. The minimum distance between the distal end of the pusher attachment and the opening may be about 3.6 cm. The minimum distance between the distal end of the pusher attachment and the opening may be about 3.5 cm. The minimum distance between the distal end of the pusher attachment and the opening may be about 3.4 cm. The minimum distance between the distal end of the pusher attachment and the opening may be about 3.3 cm. The minimum distance between the distal end of the pusher attachment and the opening may be about 3.2 cm. The minimum distance between the distal end of the pusher attachment and the opening may be about 3.1 cm. The minimum distance between the distal end of the pusher attachment and the opening may be about 2.9 cm. The minimum distance between the distal end of the pusher attachment and the opening may be about 2.8 cm. The minimum distance between the distal end of the pusher attachment and the opening may be about 2.7 cm. The minimum distance between the distal end of the pusher attachment and the opening may be about 2.6 cm. The minimum distance between the distal end of the pusher attachment and the opening may be about 2.4 cm. The minimum distance between the distal end of the pusher attachment and the opening may be about 2.3 cm. The minimum distance between the distal end of the pusher attachment and the opening may be about 2.2 cm. The minimum distance between the distal end of the pusher attachment and the opening may be about 2.1 cm. The minimum distance between the distal end of the pusher attachment and the opening may be about 2.0 cm. The minimum distance between the distal end of the pusher attachment and the opening may be about 1.9 cm. The minimum distance between the distal end of the pusher attachment and the opening may be between about 4 cm and 10 cm. The minimum distance between the distal end of the pusher attachment and the opening may be between about 5 cm and 8 cm. The minimum distance between the distal end of the pusher attachment and the opening may be between about 5 cm and 10 cm. The minimum distance between the distal end of the pusher attachment and the opening may be between about 5 cm and 9 cm. The minimum distance between the distal end of the pusher attachment and the opening may be between about 5 cm and 7 cm. The minimum distance between the distal end of the pusher attachment and the opening may be between about 5 cm and 6 cm. The minimum distance between the distal end of the pusher attachment and the opening may be between about 4 cm and 10 cm. The minimum distance between the distal end of the pusher attachment and the opening may be between about 4 cm and 9 cm. The minimum distance between the distal end of the pusher attachment and the opening may be between about 4 cm and 8 cm. The minimum distance between the distal end of the pusher attachment and the opening may be between about 4 cm and 7 cm. The minimum distance between the distal end of the pusher attachment and the opening may be between about 4 cm and 6 cm. The minimum distance between the distal end of the pusher attachment and the opening may be between about 3 cm and 12 cm. The minimum distance between the distal end of the pusher attachment and the opening may be between about 3 cm and 11 cm. The minimum distance between the distal end of the pusher attachment and the opening may be between about 3 cm and 10 cm. The minimum distance between the distal end of the pusher attachment and the opening may be between about 3 cm and 9 cm. The minimum distance between the distal end of the pusher attachment and the opening may be between about 3 cm and 8 cm.

The pusher apparatus described herein allows for the insertion of a shortened stent (the stent having a bead suspended by a tether) into a patient's ureter 90 without the need for a positioning line to withdraw the bead from the ureter 90 during positioning of the stent. Using the modified pusher apparatus described herein, the bead does not need to be pushed past the uretal orifice 85 and into the ureter 90, but remains within the pusher receptacle 17 and can stay within the bladder. Accordingly, the pusher apparatus described herein may reduce irritation to the patient's ureter and simplify the insertion, when a shortened stent with a tethered bead is used.

In accordance with one embodiment, there is provided an apparatus for the insertion of a shortened stent, said stent having a bead suspended by a tether, wherein, the pusher includes: (a) a hollow tube having a distal end and a proximal end; and (b) an opening defined in the peripheral wall of the pusher near the distal end, which reaches the inner hollow portion of the pusher and may be sized to allow for the positioning of the bead through the opening and within the receptacle defined by the opening.

In accordance with another embodiment, there is provided a pusher apparatus, for the insertion of a shortened stent, said stent having a bead suspended by a tether, wherein, the pusher includes: (a) a hollow tube having a distal end and a proximal end; and (b) an opening defined in the peripheral wall of the pusher near the distal end, which reaches the inner hollow portion of the pusher and may be sized to allow for the positioning of the bead through the opening and within the receptacle defined by the opening.

In accordance with another embodiment, there is provided a pusher apparatus, for the insertion of a shortened stent, said stent having a bead suspended by a tether, wherein, the pusher includes: (a) a hollow tube having a distal end and a proximal end; and (b) an opening defined in the peripheral wall of the pusher near the distal end, which reaches the inner hollow portion of the pusher and may be sized to allow for the positioning of the bead through the opening and within the pusher.

In accordance with another embodiment, there is provided a pusher apparatus, including: (a) a hollow tube with a distal end and a proximal end; and (b) an opening defined in the peripheral wall of the pusher near the distal end, which reaches the inner hollow portion of the pusher and may be sized to allow for positioning of a tethered bead through the opening and within the pusher.

In accordance with another embodiment, there is provided a pusher attachment apparatus, including: (a) a hollow tube having a distal end and a proximal end; (b) a connector at the proximal end of the hollow tube for attachment to a pusher having a lumen, whereby the lumen of the pusher may be contiguous with the lumen of the hollow tube; and (c) an opening defined in the peripheral wall of the hollow tube, which reaches the inner hollow portion of the hollow tube and may be sized to allow for positioning of a tethered bead through the opening and within the receptacle defined by the opening.

In accordance with another embodiment, there is provided a pusher attachment apparatus, including: (a) a hollow tube having a distal end and a proximal end; (b) a connector at the proximal end of the hollow tube for attachment to a pusher having a lumen, whereby the lumen of the pusher may be contiguous with the lumen of the hollow tube; and (c) an opening defined in the peripheral wall of the hollow tube, which reaches the inner hollow portion of the hollow tube and may be sized to allow for positioning of a tethered bead through the opening and within the pusher attachment apparatus.

In accordance with another embodiment, there is provided a commercial package including: (a) a guide wire over which a stent may be pushed; (b) a stent assembly for keeping a body channel open and having a tethered bead for stent retrieval, the stent and bead being adapted to be pushed over the guide wire; (c) a pusher attachment, as described herein, adapted to be pushed over the guide wire to advance the stent relative to the guide wire and to accept the tethered bead within the opening; and (d) a pusher tube adapted to be pushed over the guide wire for advancing the stent relative to the guide wire.

In accordance with another embodiment, there is provided a commercial package including: (a) a guide wire over which a stent may be pushed; (b) a stent assembly for keeping a body channel open and having a tethered bead for stent retrieval, the stent and bead being adapted to be pushed over the guide wire; and (c) a pusher apparatus, as described herein, adapted to be pushed over the guide wire to advance the stent relative to the guide wire and to accept the tethered bead within the opening.

In accordance with another embodiment, there is provided a commercial package including (a) a stent assembly for keeping a body channel open and having a tethered bead for stent retrieval, the stent and bead being adapted to be pushed over a guide wire; (b) a pusher attachment as described herein adapted to be pushed over the guide wire to advance the stent relative to the guide wire and to accept the tethered bead within the opening, wherein the tethered bead is retained within the opening by an holder until a guide wire is inserted; and (c) a pusher tube adapted to be pushed over the guide wire for advancing the stent relative to the guide wire.

In accordance with another embodiment, there is provided a commercial package including (a) a stent assembly for keeping a body channel open and having a tethered bead for stent retrieval, the stent and bead being adapted to be pushed over a guide wire; and (b) a pusher apparatus as described herein adapted to be pushed over the guide wire to advance the stent relative to the guide wire and to accept the tethered bead within the opening, wherein the tethered bead is retained within the opening by an holder until a guide wire is inserted.

In accordance with another embodiment, there is provided a commercial package including (a) a stent assembly for keeping a body channel open and having a tethered bead for stent retrieval, the stent and bead being adapted to be pushed over a guide wire; (b) a pusher attachment as described herein adapted to be pushed over the guide wire to advance the stent relative to the guide wire and to accept the tethered bead within the opening, wherein the tethered bead is retained within the opening by an external holder until a guide wire is inserted; and (c) a pusher tube adapted to be pushed over the guide wire for advancing the stent relative to the guide wire.

In accordance with another embodiment, there is provided a commercial package including (a) a stent assembly for keeping a body channel open and having a tethered bead for stent retrieval, the stent and bead being adapted to be pushed over a guide wire; and (b) a pusher apparatus as described herein adapted to be pushed over the guide wire to advance the stent relative to the guide wire and to accept the tethered bead within the opening, wherein the tethered bead is retained within the opening by an external holder until a guide wire is inserted.

In accordance with another embodiment, there is provided a commercial package including (a) a stent assembly for keeping a body channel open and having a tethered bead for stent retrieval, the stent and bead being adapted to be pushed over a guide wire; (b) a pusher attachment as described herein adapted to be pushed over the guide wire to advance the stent relative to the guide wire and to accept the tethered bead within the opening, wherein the tethered bead is retained within the opening by an internal holder until a guide wire is inserted; and (c) a pusher tube adapted to be pushed over the guide wire for advancing the stent relative to the guide wire.

In accordance with another embodiment, there is provided a commercial package including (a) a stent assembly for keeping a body channel open and having a tethered bead for stent retrieval, the stent and bead being adapted to be pushed over a guide wire; and (b) a pusher apparatus as described herein adapted to be pushed over the guide wire to advance the stent relative to the guide wire and to accept the tethered bead within the opening, wherein the tethered bead is retained within the opening by an internal holder until a guide wire is inserted.

The holder may internal or external or a combination of both. The holder may be a wrapper. The holder may be a mandrel.

The outer diameter of the hollow tube may be less than the diameter of the bead, provided that the pusher apparatus with a bead positioned within the receptacle is able to pass through the lumen of a cytoscope. The outer diameter of the hollow tube may be approximately the diameter of the bead. The outer diameter of the hollow tube may be greater than the diameter of the bead.

Alternatively, the outer diameter of the hollow tube may be greater than the diameter of the bead plus the cross-sectional area of the peripheral wall of the pusher opposite the opening. The outer diameter of the hollow tube may be less than the diameter of the bead plus the cross-sectional area of the peripheral wall of the pusher opposite the opening, provided that the pusher apparatus with a bead positioned within the receptacle is able to pass through the lumen of a cytoscope. The outer diameter of the hollow tube may be approximately the diameter of the bead plus the cross-sectional area of the peripheral wall of the pusher opposite the opening.

The opening may be greater than 180° of the circumference of the pusher. The opening may be greater than 185° of the circumference of the pusher. The opening may be greater than 190° of the circumference of the pusher. The opening may be greater than 195° of the circumference of the pusher. The opening may be greater than 200° of the circumference of the pusher. The opening may be greater than 205° of the circumference of the pusher. The opening may be greater than 210° of the circumference of the pusher. The opening may be greater than 210° of the circumference of the pusher. The opening may be greater than 215° of the circumference of the pusher. The opening may be greater than 220° of the circumference of the pusher. The opening may be greater than 225° of the circumference of the pusher. The opening may be greater than 230° of the circumference of the pusher. The opening may be greater than 235° of the circumference of the pusher. The opening may be greater than 240° of the circumference of the pusher. The opening may be greater than 250° of the circumference of the pusher. The opening may be greater than 255° of the circumference of the pusher. The opening may be greater than 260° of the circumference of the pusher. The opening may be greater than 265° of the circumference of the pusher. The opening may be greater than 270° of the circumference of the pusher. The opening may be greater than 280° of the circumference of the pusher. The opening may be greater than 285° of the circumference of the pusher. The opening may be greater than 290° of the circumference of the pusher. The opening may be greater than 295° of the circumference of the pusher. The opening may be greater than 300° of the circumference of the pusher. The opening may be greater than 305° of the circumference of the pusher. The opening may be greater than 310° of the circumference of the pusher. The opening may be greater than 315° of the circumference of the pusher. The opening may be greater than 320° of the circumference of the pusher. The opening may be greater than 325° of the circumference of the pusher. The opening may be greater than 330° of the circumference of the pusher. The opening may be greater than 335° of the circumference of the pusher. The opening may be greater than 340° of the circumference of the pusher. The opening may be greater than 345° of the circumference of the pusher. The opening may be greater than 350° of the circumference of the pusher. The opening may be greater than 355° of the circumference of the pusher.

The area adjacent the opening may be reinforced to maintain structural integrity of the pusher tube. The reinforcement may be by the addition of a material that is less flexible than the pusher. The reinforcement may be by the use of a material that is less flexible than the pusher tube adjacent the opening.

The minimum distance between the distal end of the pusher and the opening may be about 3 cm. The minimum distance between the distal end of the pusher and the opening may be about 2.5 cm. The minimum distance between the distal end of the pusher and the opening may be about 5.0 cm. The minimum distance between the distal end of the pusher and the opening may be about 4.9 cm. The minimum distance between the distal end of the pusher and the opening may be about 4.8 cm. The minimum distance between the distal end of the pusher and the opening may be about 4.7 cm. The minimum distance between the distal end of the pusher and the opening may be about 4.6 cm. The minimum distance between the distal end of the pusher and the opening may be about 4.5 cm. The minimum distance between the distal end of the pusher and the opening may be about 4.4 cm. The minimum distance between the distal end of the pusher and the opening may be about 4.3 cm. The minimum distance between the distal end of the pusher and the opening may be about 4.2 cm. The minimum distance between the distal end of the pusher and the opening may be about 4.1 cm. The minimum distance between the distal end of the pusher and the opening may be about 4.0 cm. The minimum distance between the distal end of the pusher and the opening may be about 3.9 cm. The minimum distance between the distal end of the pusher and the opening may be about 3.8 cm. The minimum distance between the distal end of the pusher and the opening may be about 3.7 cm. The minimum distance between the distal end of the pusher and the opening may be about 3.6 cm. The minimum distance between the distal end of the pusher and the opening may be about 3.5 cm. The minimum distance between the distal end of the pusher and the opening may be about 3.4 cm. The minimum distance between the distal end of the pusher and the opening may be about 3.3 cm. The minimum distance between the distal end of the pusher and the opening may be about 3.2 cm. The minimum distance between the distal end of the pusher and the opening may be about 3.1 cm. The minimum distance between the distal end of the pusher and the opening may be about 2.9 cm. The minimum distance between the distal end of the pusher and the opening may be about 2.8 cm. The minimum distance between the distal end of the pusher and the opening may be about 2.7 cm. The minimum distance between the distal end of the pusher and the opening may be about 2.6 cm. The minimum distance between the distal end of the pusher and the opening may be about 2.4 cm. The minimum distance between the distal end of the pusher and the opening may be about 2.3 cm. The minimum distance between the distal end of the pusher and the opening may be about 2.2 cm. The minimum distance between the distal end of the pusher and the opening may be about 2.1 cm. The minimum distance between the distal end of the pusher and the opening may be about 2.0 cm. The minimum distance between the distal end of the pusher and the opening may be about 1.9 cm. The minimum distance between the distal end of the pusher and the opening may be between about 4 cm and 10 cm. The minimum distance between the distal end of the pusher and the opening may be between about 5 cm and 8 cm. The minimum distance between the distal end of the pusher and the opening may be between about 5 cm and 10 cm. The minimum distance between the distal end of the pusher and the opening may be between about 5 cm and 9 cm. The minimum distance between the distal end of the pusher and the opening may be between about 5 cm and 7 cm. The minimum distance between the distal end of the pusher and the opening may be between about 5 cm and 6 cm. The minimum distance between the distal end of the pusher and the opening may be between about 4 cm and 10 cm. The minimum distance between the distal end of the pusher and the opening may be between about 4 cm and 9 cm. The minimum distance between the distal end of the pusher and the opening may be between about 4 cm and 8 cm. The minimum distance between the distal end of the pusher and the opening may be between about 4 cm and 7 cm. The minimum distance between the distal end of the pusher and the opening may be between about 4 cm and 6 cm. The minimum distance between the distal end of the pusher and the opening may be between about 3 cm and 12 cm. The minimum distance between the distal end of the pusher and the opening may be between about 3 cm and 11 cm. The minimum distance between the distal end of the pusher and the opening may be between about 3 cm and 10 cm. The minimum distance between the distal end of the pusher and the opening may be between about 3 cm and 9 cm. The minimum distance between the distal end of the pusher and the opening may be between about 3 cm and 8 cm. The minimum distance between the distal end of the pusher and the opening may be between about 2 cm and 10 cm.

The minimum distance between the distal end of the pusher attachment and the opening may be about 3 cm. The minimum distance between the distal end of the pusher attachment and the opening may be about 2.5 cm. The minimum distance between the distal end of the pusher attachment and the opening may be about 5.0 cm. The minimum distance between the distal end of the pusher attachment and the opening may be about 4.9 cm. The minimum distance between the distal end of the pusher attachment and the opening may be about 4.8 cm. The minimum distance between the distal end of the pusher attachment and the opening may be about 4.7 cm. The minimum distance between the distal end of the pusher attachment and the opening may be about 4.6 cm. The minimum distance between the distal end of the pusher attachment and the opening may be about 4.5 cm. The minimum distance between the distal end of the pusher attachment and the opening may be about 4.4 cm. The minimum distance between the distal end of the pusher attachment and the opening may be about 4.3 cm. The minimum distance between the distal end of the pusher attachment and the opening may be about 4.2 cm. The minimum distance between the distal end of the pusher attachment and the opening may be about 4.1 cm. The minimum distance between the distal end of the pusher attachment and the opening may be about 4.0 cm. The minimum distance between the distal end of the pusher attachment and the opening may be about 3.9 cm. The minimum distance between the distal end of the pusher attachment and the opening may be about 3.8 cm. The minimum distance between the distal end of the pusher attachment and the opening may be about 3.7 cm. The minimum distance between the distal end of the pusher attachment and the opening may be about 3.6 cm. The minimum distance between the distal end of the pusher attachment and the opening may be about 3.5 cm. The minimum distance between the distal end of the pusher attachment and the opening may be about 3.4 cm. The minimum distance between the distal end of the pusher attachment and the opening may be about 3.3 cm. The minimum distance between the distal end of the pusher attachment and the opening may be about 3.2 cm. The minimum distance between the distal end of the pusher attachment and the opening may be about 3.1 cm. The minimum distance between the distal end of the pusher attachment and the opening may be about 2.9 cm. The minimum distance between the distal end of the pusher attachment and the opening may be about 2.8 cm. The minimum distance between the distal end of the pusher attachment and the opening may be about 2.7 cm. The minimum distance between the distal end of the pusher attachment and the opening may be about 2.6 cm. The minimum distance between the distal end of the pusher attachment and the opening may be about 2.4 cm. The minimum distance between the distal end of the pusher attachment and the opening may be about 2.3 cm. The minimum distance between the distal end of the pusher attachment and the opening may be about 2.2 cm. The minimum distance between the distal end of the pusher attachment and the opening may be about 2.1 cm. The minimum distance between the distal end of the pusher attachment and the opening may be about 2.0 cm. The minimum distance between the distal end of the pusher attachment and the opening may be about 1.9 cm. The minimum distance between the distal end of the pusher attachment and the opening may be between about 4 cm and 10 cm. The minimum distance between the distal end of the pusher attachment and the opening may be between about 5 cm and 8 cm. The minimum distance between the distal end of the pusher attachment and the opening may be between about 5 cm and 10 cm. The minimum distance between the distal end of the pusher attachment and the opening may be between about 5 cm and 9 cm. The minimum distance between the distal end of the pusher attachment and the opening may be between about 5 cm and 7 cm. The minimum distance between the distal end of the pusher attachment and the opening may be between about 5 cm and 6 cm. The minimum distance between the distal end of the pusher attachment and the opening may be between about 4 cm and 10 cm. The minimum distance between the distal end of the pusher attachment and the opening may be between about 4 cm and 9 cm. The minimum distance between the distal end of the pusher attachment and the opening may be between about 4 cm and 8 cm. The minimum distance between the distal end of the pusher attachment and the opening may be between about 4 cm and 7 cm. The minimum distance between the distal end of the pusher attachment and the opening may be between about 4 cm and 6 cm. The minimum distance between the distal end of the pusher attachment and the opening may be between about 3 cm and 12 cm. The minimum distance between the distal end of the pusher attachment and the opening may be between about 3 cm and 11 cm. The minimum distance between the distal end of the pusher attachment and the opening may be between about 3 cm and 10 cm. The minimum distance between the distal end of the pusher attachment and the opening may be between about 3 cm and 9 cm. The minimum distance between the distal end of the pusher attachment and the opening may be between about 3 cm and 8 cm. The minimum distance between the distal end of the pusher attachment and the opening may be between about 2 cm and 10 cm.

The tether connecting the bead and the stent, may be made available in variable diameters. Particularly, in the event that drainage would be useful. For example, occasionally, after the ureter has been traversed with an instrument it may be traumatized causing edema and obstruction of the urinary flow. When there is swelling in the intramural (bladder portion) of the ureter, drainage of the ureter may assist with reducing the swelling. Generally, a stent will allow for drainage of the ureter, but in some instances the swelling may be such that the stent alone is not sufficient to provide drainage, in particular, where a shortened stent is used. In such circumstances the tether may also assist with drainage of the ureter. A larger diameter tether or possibly even a flat tether may help with drainage. Alternatively, tether with other non-circular cross-sections may be appropriate in the circumstances.

BRIEF DESCRIPTION OF THE DRAWINGS

In drawings which illustrate embodiments of the invention.

DETAILED DESCRIPTION

As used herein a "bead" is meant to include any ferromagnetic member. Ferromagnetic as used herein is meant to include materials which may comprised of iron, nickel, chromium, or cobalt or combinations thereof and various alloys, such that the bead is attracted to a magnet. For example, a bead may be made from ferromagnetic stainless steel. Furthermore, beads are preferably biocompatible. For example, a stainless steel bead may be coated with a smooth layer of polymer, for example, polytetrafluoroethylene. A "biocompatible" bead or a bead coated with a biocompatible coating, may prevent the reaction of the bead with urine or bile, or other bodily fluids in which the bead may be placed. Furthermore, the bead may itself be a magnet. Beads as described herein are generally biocompatible, rounded, perforated, and ferromagnetic. For example, a bead may be made from a rare earth magnet or a stainless steel having magnetic properties.

A pusher is essentially a hollow tube, which may be made in a variety of diameters and having a range of wall thicknesses, and may be selected to ensure compatibility for use with a given stent. A pusher may be made from high durometer (stiff), biocompatible, polymers and polymer blends (for example, polyurethane, high density polyethylene, nylon, etc. and blends thereof), as known in the art.

A holder as used herein, is meant to include any member that is capable of retaining a bead within an opening of a modified pusher apparatus or a pusher attachment, to facilitate the insertion of a guide wire through the bead, while the bead is within the opening of the modified pusher apparatus or the pusher attachment. The holder may be removed after insertion of a guide wire or may remain associated with the modified pusher apparatus or the pusher attachment, but be in a release position so that when the guide wire is removed during s stent insertion, the bead may be released from the modified pusher apparatus or the pusher attachment. A commercial package containing such a holder, may facilitate loading of a selected guide wire, for insertion into the apparatus. A holder may be internal or external or a combination thereof. Furthermore, a holder may, for example, take the form of a removable wrapper, a clip, a mandrel, a wedge, an adhesive surface modification etc. An adhesive surface modification, may be prepared such that the adhesive dissolves when in situ (for example, in urine, at body temperature, etc.). Such a system allows for the selection of the best guide wire to suit the patient or the personal preferences of the user. For example, guide wires may be chosen for their frictional properties (for example, a hydrophilic coating may provide for less friction) or their 'pushability'.

A mandrel, as used herein, may be a wire that resides within the modified pusher apparatus or a pusher attachment, to hold the bead within the opening of the modified pusher apparatus or the pusher attachment until the guide wire is inserted. The mandrel may be sized to fit within the bead with the guide wire or such that it is pushed out of the bead as the guide wire is inserted.

A wrapper, as used herein, may be any type of protective covering that is capable of retaining a bead within the opening of a modified pusher apparatus or a pusher attachment, to facilitate the insertion of a guide wire through the bead. Such a wrapper may be removed once the guide wire is inserted through the bead.

Figure 1:
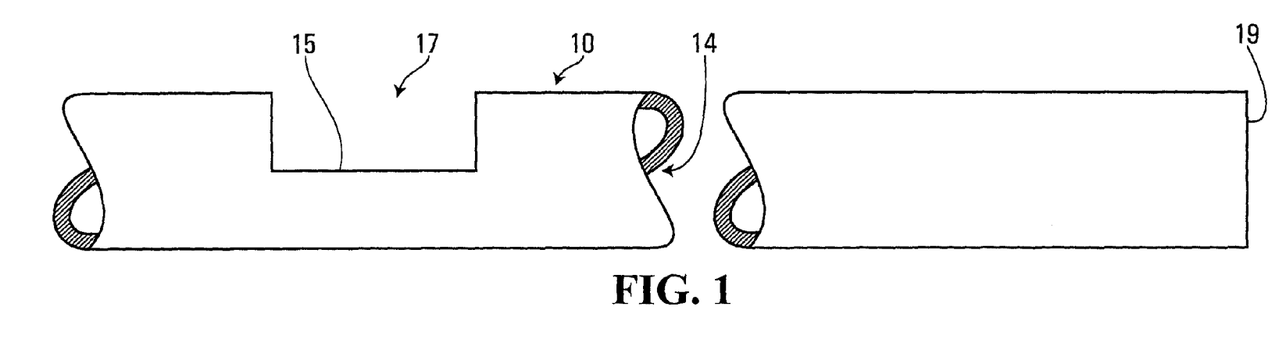
FIG. 1 is a side view of a modified pusher apparatus according to a first embodiment.

Referring to FIG. 1, a modified pusher apparatus according to a first embodiment is shown generally at 10. The inner hollow portion or lumen of the pusher is shown at 14 and the distal end of the modified pusher apparatus is shown at 19. The modified pusher apparatus has a receptacle 17, which is defined by an opening 15. The lumen of the pusher may receive a guide wire (not shown in FIG. 1) and the receptacle 17 is sized and positioned near the distal end of the pusher 19 to receive a tethered bead attached to the proximal end of the stent (the bead and stent are not shown in FIG. 1).

Figure 2:
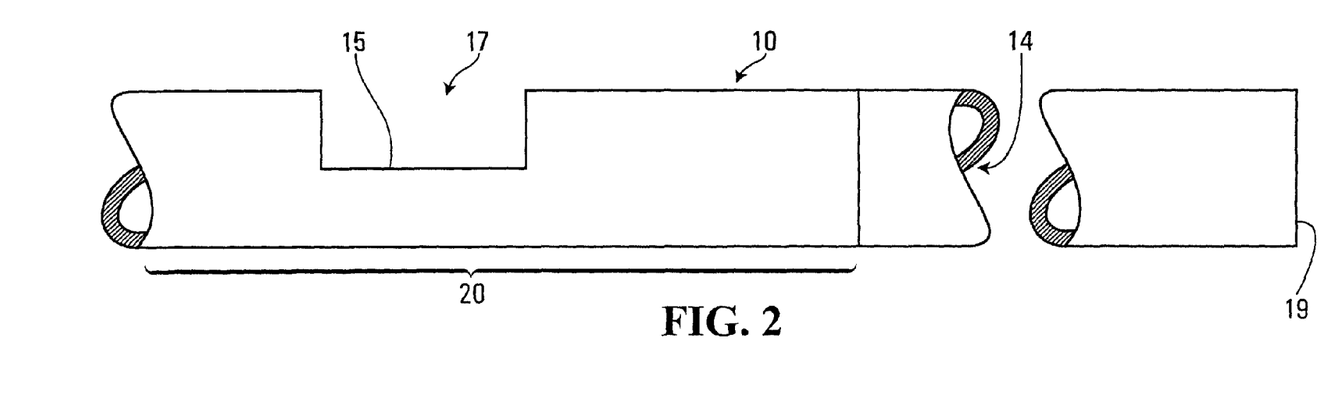
FIG. 2 is a side view of a modified pusher apparatus according to a second embodiment, wherein the area adjacent the opening is reinforced.

Referring to FIG. 2, a modified pusher apparatus according to a second embodiment is shown generally at 10. Similar to FIG. 1, the inner hollow portion or lumen of the pusher is shown at 14 and the distal end of the modified pusher apparatus is shown at 19. The modified pusher apparatus has a receptacle 17, which is defined by an opening 15. The lumen of the pusher may receive a guide wire (not shown in FIG. 2) and the receptacle 17 is sized and positioned near the distal end of the pusher 19 to receive a tethered bead attached to the proximal end of the stent (the bead and stent are not shown in FIG. 2). However, the modified pusher of FIG. 2 has a reinforced area 20 adjacent the opening to maintain the structural integrity of the pusher tube despite the opening 15 in the wall of the pusher tube. The reinforced area 20 may be made of a different material than the remainder of the pusher or the reinforced area 20 may have added material that is the same as or different than the remainder of the pusher. Furthermore, the reinforced area 20 may be made of a material that is less flexible than the remainder of the pusher or the reinforced area 20 may have added material that is less flexible than the remainder of the pusher. The reinforcement applied in the reinforced area 20 adjacent the opening and the size of the area to be reinforced 20 may depend on a number of factors, which may include the size of the opening 15, the shape of the opening 15, the properties of the material from which the remainder of the pusher is made, the properties of the material adjacent the opening 15, the properties of the material defining the borders of the receptacle 17, and the use in which the pusher is to be implemented. In view of the above a person of skill in the art would be well aware of the reinforcement that may be applied to maintain the structural integrity of the pusher. The reinforced area, for example, may be made from stainless steel or another alloy.

Figure 3:
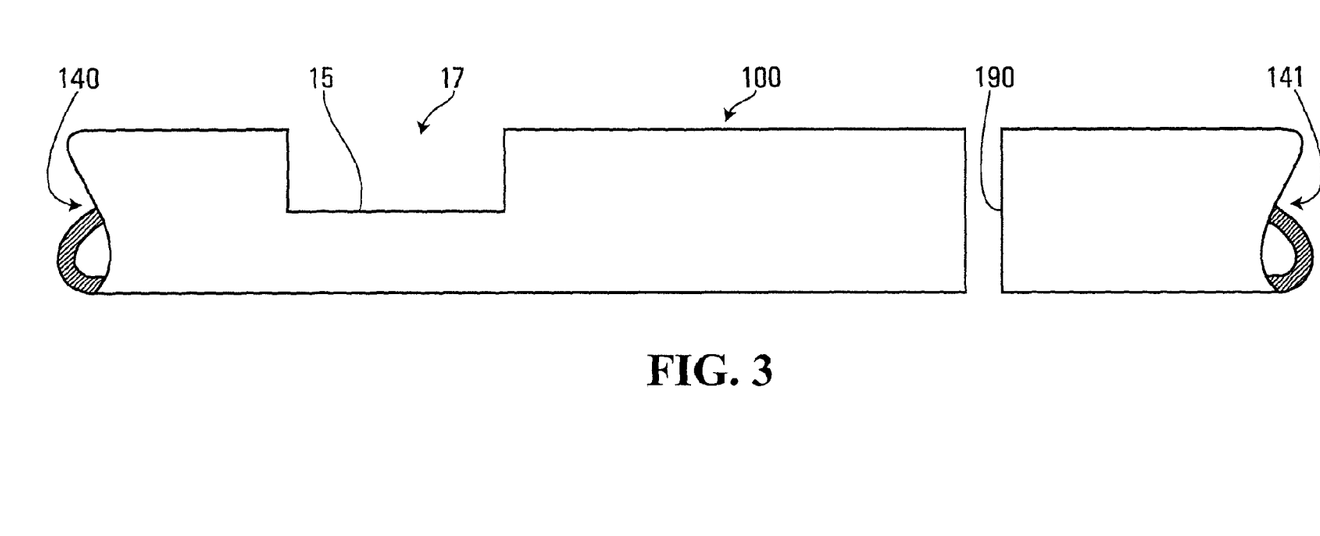
FIG. 3 is a side view of a pusher attachment apparatus according to an embodiment adjacent to an unmodified pusher.

Referring to FIG. 3, a pusher attachment apparatus according to an embodiment is generally shown at 100. The inner hollow portion or lumen of the pusher attachment apparatus is shown at 140, the inner hollow portion or lumen of the pusher is shown at 141, and the distal end of the pusher apparatus is shown at 190. The pusher attachment apparatus has a receptacle 17, which is defined by an opening 15. The lumen of the pusher may receive a guide wire (not shown in FIG. 3) and the receptacle 17 is sized and positioned to receive a tethered bead attached to the proximal end of the stent (the bead and stent are not shown in FIG. 3). The pusher attachment apparatus may be designed, to be attached to any standard pusher apparatus to allow for the positioning of a bead, which is tethered to a stent, within the receptacle 17.

Figure 4:
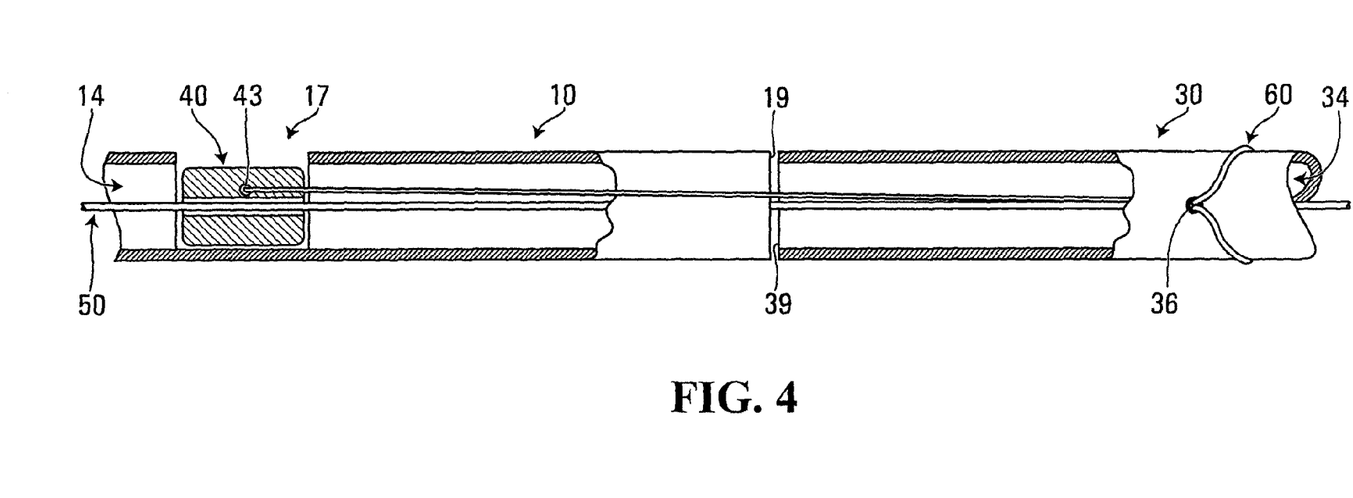
FIG. 4 is a partial cross-sectional view of the modified pusher apparatus of FIG. 1, adjacent to a stent assembly having a tether and a bead, all threaded over a guide wire, wherein the bead is positioned within the opening of the modified pusher apparatus.

Referring to FIG. 4, a modified pusher apparatus according to a first embodiment is shown in a partial cross-section generally at 10, adjacent a partial cross-section of a shortened stent 30. The stent 30 is positioned along a guide wire 50 at the distal end 19 of the modified pusher 10, whereby the distal end 19 of the modified pusher 10 is adjacent to the proximal end 39 of the stent 30. The guide wire 50 is shown, from proximal to distal (left to right), passing through the inner hollow portion or lumen 14 of the modified pusher apparatus 10, passing through the bore or perforation in the bead 40, through the remainder of the lumen 14 of the modified pusher apparatus 10, and passing through the inner hollow portion or lumen 34 of the stent 30. The modified pusher apparatus has a receptacle 17, which is defined by an opening 15. The bead 40 is shown positioned near the distal end of the pusher 19, within the receptacle 17 and with the guide wire passing through the bore within the bead. A tether 60 is shown looping around the exterior of the stent and passing through a stent perforation 36, passing through the inner hollow portion or lumen 34 of the stent 30 to the proximal end of the stent 39, then along the outer surface of the modified pusher apparatus 10, to the bead 40 and through the tether opening 43 of the bead, wherein the tether opening as shown is generally extend through the bead perpendicular to the long axis of the bead. As shown in FIG. 4, only one side of the tether loop is shown between the bead and the stent lumen.

Figure 5:
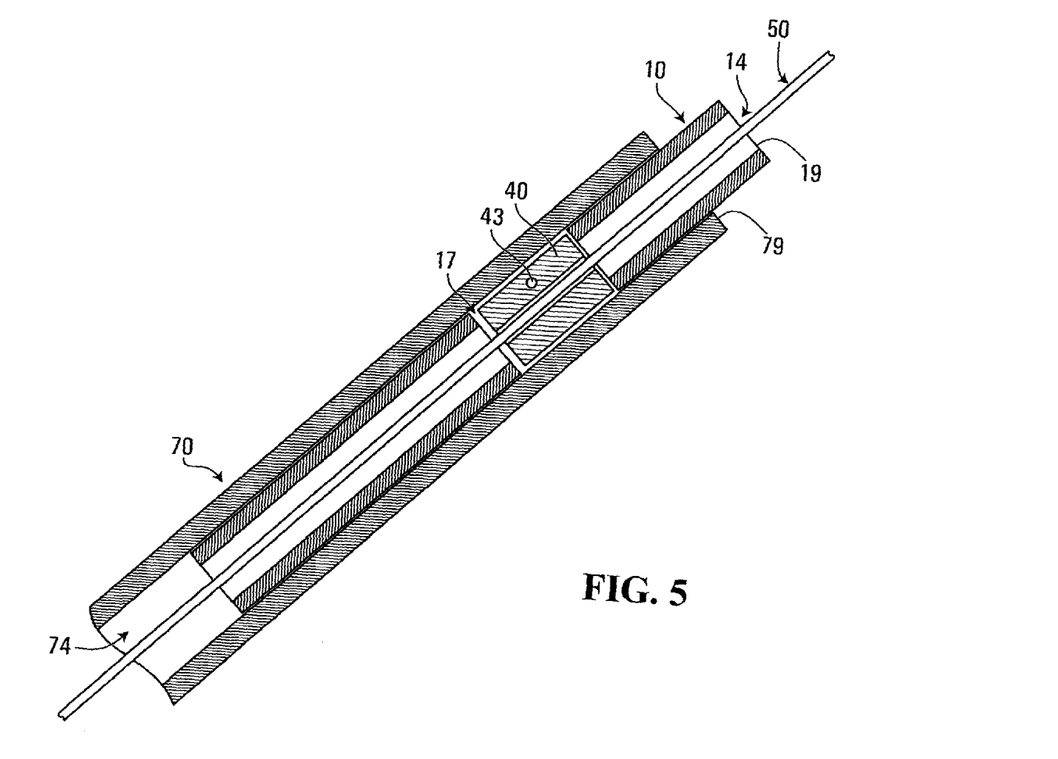
FIG. 5 is a cross-sectional view of the modified pusher apparatus of FIG. 1, positioned within a cytoscope, threaded over a guide wire, with a bead positioned within the opening of the modified pusher apparatus.

Referring to FIG. 5, a modified pusher apparatus according to a first embodiment is shown in a partial cross-section generally at 10, positioned within the lumen 74 of a cytoscope 70. The bead 40 is shown in cross-section positioned within the receptacle 17 adjacent the distal end 19 of the modified pusher 10, whereby the distal end 19 of the modified pusher 10 is adjacent to the distal end 79 of the cytoscope 70. Also shown, is the bead tether opening 43, but the tether is not shown. The guide wire 50 is shown, from proximal to distal (bottom left to top right), passing through the inner hollow portion or lumen 14 of the modified pusher apparatus and through the lumen of the cytoscope 74, passing through the bore or perforation in the bead 40, through the remainder of the lumen 14 of the modified pusher apparatus 10, and passing through the inner hollow portion or lumen 34 of the stent 30.

Figure 6:
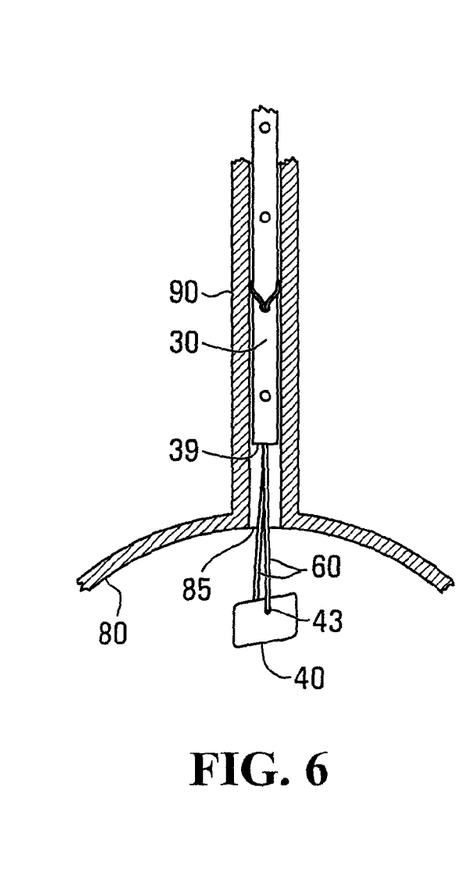
FIG. 6 illustrates a shortened stent positioned within the ureter and a tethered bead suspended in the bladder.
Figure 7:
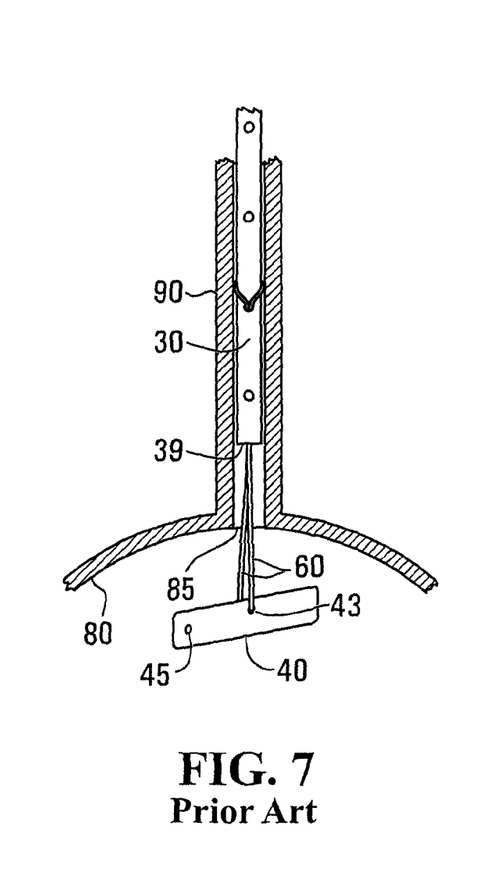
FIG. 7 illustrates a shortened stent positioned within the ureter and a prior art tethered bead suspended in the bladder.
Figure 8:
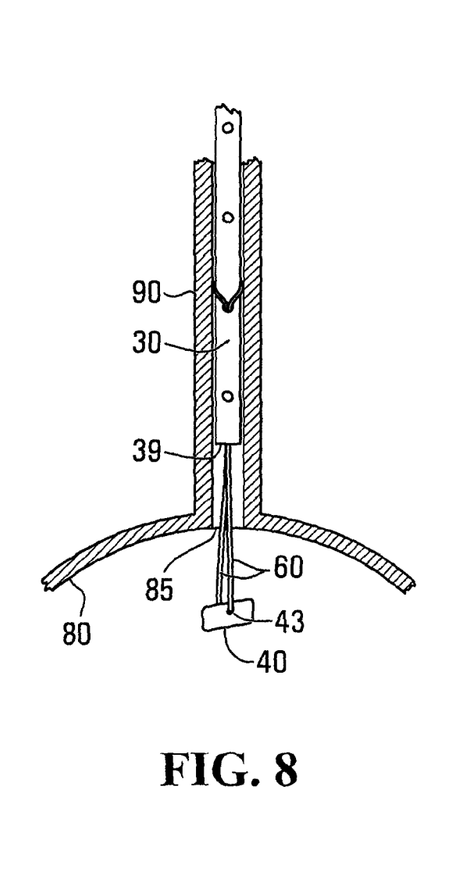
FIG. 8 illustrates a shortened stent positioned within the ureter and a larger tethered bead than in FIG. 6, suspended in the bladder.

Referring to FIGS. 6, 7, and 8, shortened stents are shown positioned within the ureter 90, following insertion with the insertion apparatus removed (i.e. cytoscope, pusher and guidewire). The stent assembly, which includes the shortened perforated stent 30, tether 60, and bead 40 are shown in FIGS. 6, 7, and 8 with three different bead designs. The bead design in FIG. 7 is reproduced from the PCT application PCT/CA99/00405. The positioning of the stent assembly is such that the proximal end of the stent 39 is positioned within the ureter 90 and away from the ureteral orifice 85 and whereby the bead 40 is suspended in the bladder 80 by the tether 60, which passes through the bead tether opening 43. FIG. 7 also shows a passage for a positioning line 45 within the bead (positioning line not shown). FIG. 6 shows a larger bead design relative to FIG. 8. Nevertheless, the shorter bead designs of FIGS. 6 and 8 may permit better rotation on the tether, as compared to the bead of FIG. 7, which may assist in release of the tethered bead from the pusher apparatus or pusher attachment (not shown in FIGS. 6-8).

Referring to FIGS. 4-8, the bead tether opening 43 as shown is generally at a midpoint in the bead 40 to allow the bead to lie perpendicular to the ureteric orifice 85 and prevent migration up the ureter 90.

The operation of the modified pusher apparatus for the insertion of a shortened stent 30 into a ureter 90 may be described as follows:

- a cytoscope 70 is inserted into the bladder, and a guide wire 50 is passed up the cytoscope lumen 74 to the bladder and up the ureter into a kidney;
- a shortened stent 30 is threaded onto the guide wire 50, without threading the bead 40, followed by the modified pusher apparatus 10 until the guide wire approaches the receptacle 17,
- the bead 40 tethered to the stent 39 is positioned within the receptacle 17 such that the guide wire 50 may pass through the bead and towards the proximal end of the pusher (alternatively, the stent 30, pusher 10, bead 40 and guidewire 50 may be preassembled to allow for insertion as a unit);
- the shortened stent 30 followed by the modified pusher apparatus 10, with the bead 40 positioned within the receptacle 17 and held in place by the guide wire, are advanced up the guide wire 50 and through the cytoscope 70 into the bladder 80;
- the shortened stent 30 and the modified pusher apparatus 10 are further advanced up the ureter so that the hook or pigtail (not shown) on the distal end of the stent is positioned within the kidney and the proximal end of the stent 39 is positioned within the ureter 90 as shown in FIGS. 6-8;
- the cytoscope 70, which is situated in the bladder 80, is used to visually confirm (fluoroscopic confirmation) the correct positioning of the stent 30 based on the position of the modified pusher apparatus 10 relative to the uretal orifice 85 (such a fluoroscopic confirmation may be simplified, where the pusher has markings or gradations so that the operator can gauge the depth of the stent within the ureter);
- the modified pusher apparatus 10 is held in position adjacent the proximal end of the stent 39, while the guide wire 50 is removed so that the shortened stent 30 does not slide down the ureter 90 (from distal to proximal) as the guide wire is withdrawn from the ureter; and
- the modified pusher apparatus 10 is withdrawn into the cystoscope and removed together with the cytoscope 70 (to avoid damaging the urethra with the receptacle 17).

Removal of the stent 30 may be accomplished by a non-surgical procedure that does not even require endoscopy. As described in an earlier patent application (WO99/58083) a retrieval catheter (not shown), which comprises a conventional catheter that is modified to mount a magnet at the distal tip of the catheter. The magnet may also be covered with a biocompatible coating and/or may be rounded to prevent injury to the patient. The magnet-tipped end of the retrieval catheter is inserted, through the urethra and into the bladder, where the catheter tip magnetically engages the suspended bead 40. As the catheter is withdrawn the bead 40 and tether-connected stent 30 are pulled from the ureter and explanted from the patient.

As the retrieval catheter approaches the bead 40, the magnetic flux acting on the bead 40 should be sufficient to cause the bead to rotate relative to the tether from its normal, suspended position, so that one of the ends of the bead 40 rotates on the tether to contact the tip of the retrieval catheter. Accordingly, the bead will be oriented generally coaxially with the end of the retrieval catheter. If this orientation is not attained in the bladder, as the retrieval catheter and bead enter the urethra passage, the urethra will likely cause the axial alignment of the bead 40 with the retrieval catheter, which is desired for comfortable removal of the bead through the urethra. It will be appreciated that this rotation of the bead will be assured where the bead is magnetized, and one of its ends has a polarity opposite that of the magnet on the retrieval catheter.

Alternatively, the bead 40 could be a magnet and the retrieval catheter tipped with ferromagnetic material or another magnet. Although a rare-earth magnet is preferred, other types, including electromagnets could be employed with the retrieval catheter. In addition, the bead may be of a more ball shape FIGS. 6 and 8, rather than the elongated bead of FIG. 7.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A pusher apparatus, for the insertion of a shortened stent,
    wherein, the pusher apparatus comprises:
    (a) a hollow tube having a distal end and a proximal end, wherein the hollow tube has a diameter similar to or the same as the diameter of the shortened stent, such that the distal end of the pusher is adapted to be positioned adjacent the proximal end of the shortened stent; and
    (b) an opening defined in a peripheral wall of the pusher apparatus near the distal end, where the opening reaches a hollow portion of the pusher apparatus to form a receptacle and the receptacle is sized to allow for the positioning therein of a ferromagnetic bead tethered to the shortened stent, where the ferromagnetic bead has a bore therethrough, such that when the bead is positioned within the receptacle, the bore is coaxial with the hollow tube, such that a guide wire extending longitudinally through the pusher apparatus can pass through the bore of the tethered ferromagnetic bead,
    wherein removal of the guide wire from the bore facilitates release of the ferromagnetic bead from the receptacle.

2. The pusher apparatus of claim 1, wherein the outer diameter of the hollow tube is greater than the diameter of the bead and the cross-sectional area of the peripheral wall of the pusher opposite the opening.

3. The pusher apparatus of claim 1, wherein the opening is greater than 180° of the circumference of the pusher.

4. The pusher apparatus of claim 1, wherein the area adjacent the opening is reinforced to maintain structural integrity of the pusher tube.

5. The pusher apparatus of claim 4, wherein the reinforcement comprises a material that is different from the material of the pusher apparatus.

6. The pusher apparatus of claim 1, wherein the minimum distance between the distal end of the pusher and the opening is between about 2 cm and about 10 cm.

7. The pusher apparatus of claim 1, wherein the minimum distance between the distal end of the pusher and the opening is between about 4 cm and about 10 cm.

8. The pusher apparatus of claim 1, wherein the minimum distance between the distal end of the pusher and the opening is between about 5 cm and about 8 cm.

9. The pusher apparatus of claim 1, wherein the minimum distance between the distal end of the pusher and the opening is between about 5 cm and about 7 cm.

10. The pusher apparatus of claim 1, wherein the minimum distance between the distal end of the pusher and the opening is between about 5 cm and about 6 cm.

11. The pusher apparatus of claim 1, wherein the minimum distance between the distal end of the pusher and the opening is about 3 cm.

12. The pusher apparatus of claim 1, wherein the minimum distance between the distal end of the pusher and the opening is about 2 cm.

\* \* \* \* \*